(12) United States Patent
Wilson

(10) Patent No.: US 6,231,341 B1
(45) Date of Patent: May 15, 2001

(54) DENTAL MATRIX TENSIONER

(76) Inventor: Jerry Don Wilson, P.O. Box 271, Crescent City, CA (US) 95531

( * ) Notice: Subject to any disclaimer, the term of this patent is extended or adjusted under 35 U.S.C. 154(b) by 0 days.

(21) Appl. No.: 09/664,214

(22) Filed: Sep. 18, 2000

(51) Int. Cl.[7] .................................................... A61C 5/04
(52) U.S. Cl. ............................................. 433/155; 433/39
(58) Field of Search ............................. 433/39, 40, 155, 433/156, 157

(56) References Cited

U.S. PATENT DOCUMENTS

| | | | |
|---|---|---|---|
| 698,280 | * | 4/1902 | Hinker .................................... 433/39 |
| 2,367,439 | * | 1/1945 | Samphere .............................. 433/155 |
| 2,502,903 | * | 4/1950 | Tofflemire . |
| 2,611,182 | * | 9/1952 | Tofflemire .............................. 433/39 |
| 2,687,573 | * | 8/1954 | Stone . |
| 2,709,302 | * | 5/1955 | Reiter . |
| 3,020,638 | * | 2/1962 | Tofflemire ............................ 433/155 |
| 5,722,831 | * | 3/1998 | Lin ........................................ 433/155 |

* cited by examiner

Primary Examiner—Ralph A. Lewis
(74) Attorney, Agent, or Firm—Linval B. Castle

(57) ABSTRACT

A lingual dental matrix tensioner comprising two posts maintained parallel by two parallel rods through the posts at a right angle to the post axes One rod is threaded and has an end knob for adjusting the spacing between the posts, the other rod is a guide rod. Both ends of a matrix band are clamped to one post and the doubled matrix is guided through one of several slots in the other to form a retainer loop at any location. Rotating the threaded rod to separate the posts reduces the size of the loop.

6 Claims, 2 Drawing Sheets

DENTAL MATRIX TENSIONER

BRIEF SUMMARY OF THE INVENTION

This invention relates to dental tools and particularly to a matrix band holder and tensioner that is used from a position on the lingual side of the teeth.

The matrix tensioners have been used by dentists for many years for encircling and tightening a very thin metal matrix band around teeth in preparation for tooth filling procedures. These matrix tensioners are small devices that rests of the labial side of the teeth and which clamp the ends of a matrix band to form a loop which may be tightened to form a metal retainer around a tooth so that the dentist can compress filling material into the tooth.

Heretofore, matrix tensioners have been applied on and labial side of the tooth between the gums and the lips so that, when working with the rear molars, the dentist's working space was restricted and the patient suffered discomfort. The matrix tensioner to be described is designed for retaining on the lingual side of the teeth, thus providing the dentist with ample working space and causing less discomfort for the patient.

Briefly described the lingual matrix tensioner includes two parallel, spaced posts, each less than one centimeter in diameter and about two centimeters in length. Both ends of a metal matrix band are clamped to one of the posts and the doubled matrix passes through various slots in the lower third of each post so that a matrix loop is produced at various locations at the other post. The spacing between the two posts is adjusted by a rotatable rod which is anchored to one post and threaded through the other so that rotation of the rod causes separation of two posts and a reduction in the size of the matrix loop.

BRIEF DESCRIPTION OF THE DRAWINGS

In the drawings which illustrate a preferred embodiment of the dental matrix tensioner

DETAILED DESCRIPTION

A matrix is a tissue-thin stainless steel band that tightened around a tooth or group of teeth so that the dentist can compress material into the tooth without it squeezing out. There are numerous types of matrix holders or matrix tensioners that tighten a matrix band around a tooth but these are labial matrix holders designed to be operated from the front of the jaw where they become a working obstacle for the dentist. The matrix holder of the invention is a lingual matrix holder or tensioner so that, in its position behind the teeth, it is out of the dentist's way and is not a working obstacle.

Figure 1:
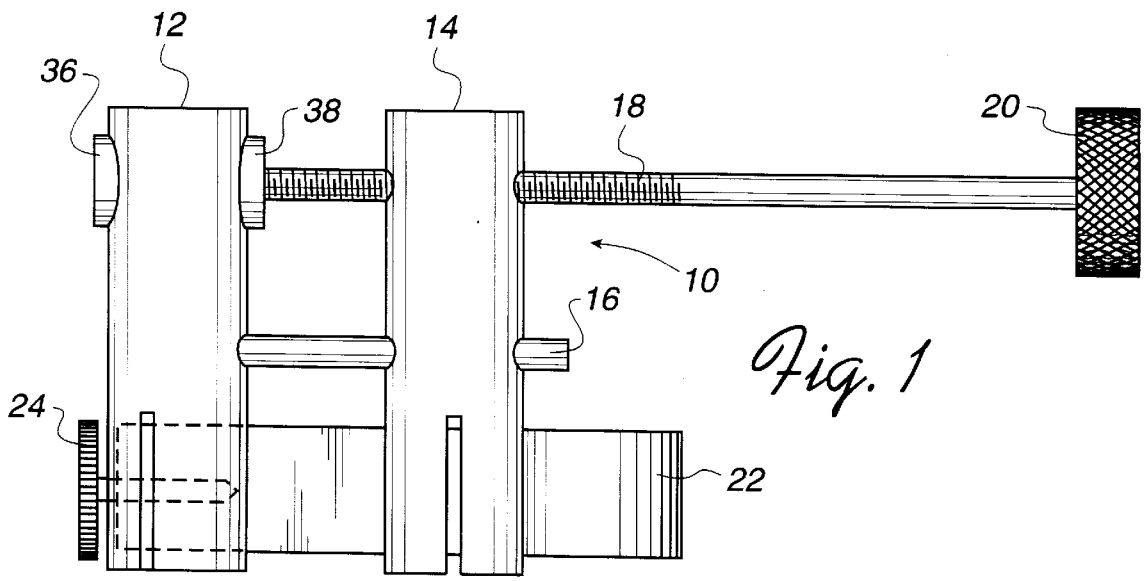
FIG. 1 is a side elevational view of the tensioner with matrix installed.

FIG. 1 is a side elevational view of the lingual matrix tensioner 10 which comprises two identical parallel posts 12, 14 radially connected by two parallel rods at a right angle through the diameters of the posts: a guide rod 16 having one end anchored in post 12 and slideable through post 14, and a threaded rod 18 having one end rotatably anchored in post 12 and threaded through threads in post 14. A knurled handle 20 is on the end of the threaded rod 18 opposite the post 12.

The posts are preferable solid stainless steel cylinders approximately one inch long and ¼ inch in diameter. The guide rod 16 is approximately centered and the threaded rod 18 is near the top of the posts. Approximately one third up from the bottom of each post 12, 14 is slotted for the passage of a double thickness of the matrix band 22 which is formed into a loop that passes through selected slots in the bottom of the posts and has its free ends attached to the post 12 by a locking screw 24 as shown in FIG. 1.

Figure 2:
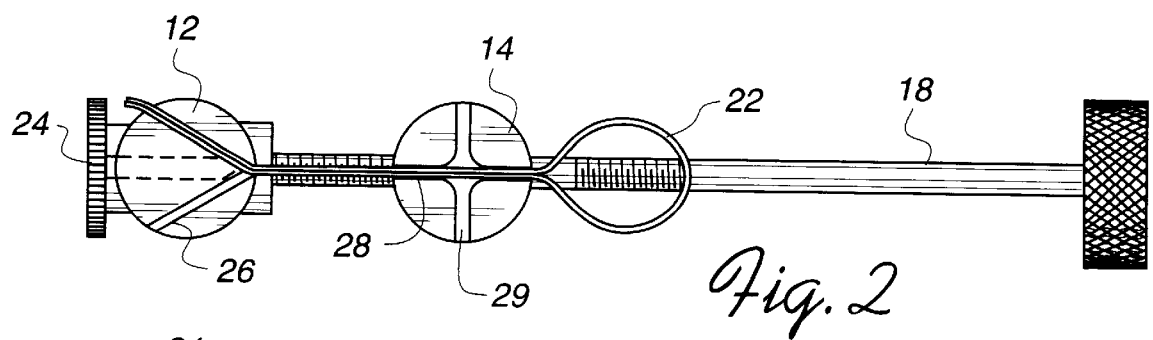
FIG. 2 is a bottom plan view thereof.

FIG. 2 is a bottom plan view of the tensioner showing the slot detail in the bottom of each post 12, 14. The locking screw 24 is threaded into the post 12 near the bottom surface and on an axis parallel with the axis of the adjustment screw 18 and guide rod 16. The screw 24 is threaded into a hole that is drilled and tapped through the post at a point approximately half way between the bottom surface of the post and the top of the slots cut in the post for the passage of the matrix band. The slot 26 in the bottom of the post 12 is in the form of a "V". The locking screw 24 is positioned midway between the legs of the "V" with its end in the apex of the "V", clamping the matrix band. The width of each leg of the V slot must be adequate to pass two thicknesses of the matrix band.

The bottom of post 14 is also slotted but with an axial cross, the first leg 28 of which is on an axis parallel with the adjustment screw 18, the second leg 29 being transverse at a right angle to the first leg 28. The width of both legs 28, 29 of the slot must be adequate to easily pass a double thickness of the matrix band. It is recommended that the interior intersection of the legs 29, 29 are rounded, as shown, to further reduce friction as the matrix is being tightened if the dentist elects to guide the matrix band through both the first leg 28 and the transverse leg 29.

Figure 3:
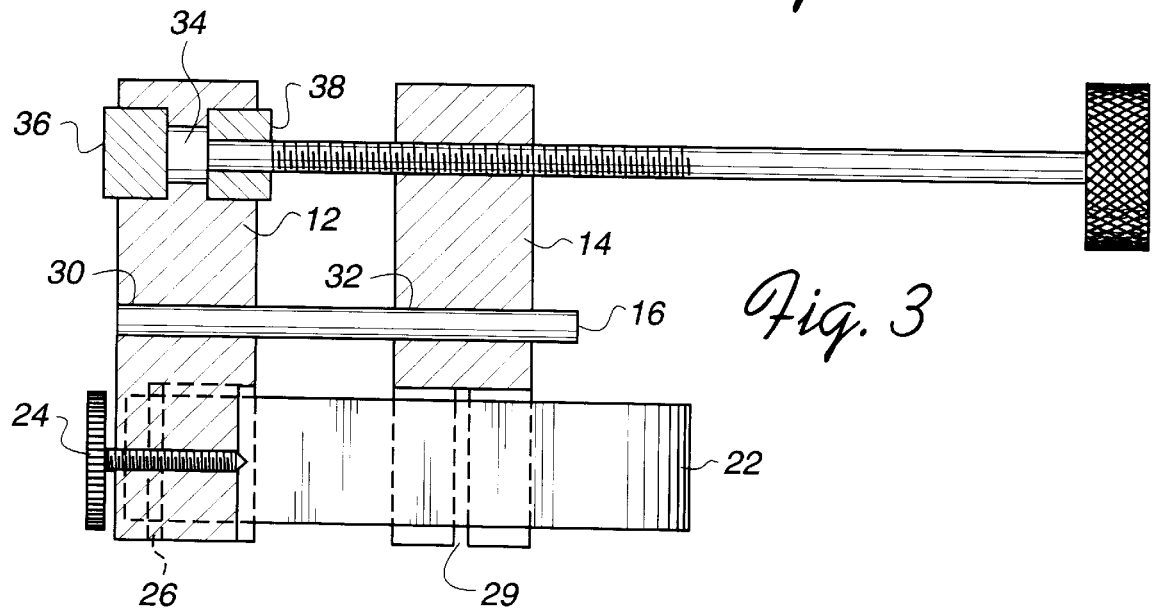
FIG. 3 is a sectional side elevational view thereof.

FIG. 3 is a sectional elevational view of the matrix tensioner 10 showing the construction of the preferred embodiment. The two posts 12, 14 which may be solid cylinders have the slots 26, 28, 29 and the locking screw 24 in the approximate lower third, the guide rod 16 through the diameter of the posts at the center, and the adjustment screw 18 through the diameter of the posts as near as possible to the top surface. The matrix is at the lowest part of the tensioner 10 and the guide rod 16, located above the matrix, must be sufficiently above the matrix so it will not contact the top surface of the teeth. Therefore the length of the posts from their bottom ends to the guide rod 16 must be greater than the length of the patient's teeth.

The guide rod 16 is tightly attached in hole 30 through the post 12 and is slideably engaged in hole 32 through the post 14 so that post 14 may be moved toward and away from post 12. The adjustment screw 18 has a hub 34 within the post 12 which is locked against all lateral movement but which permits rotational movement of the screw by the strong washers 36, 38 that screw or are tightly pressed into the post 12.

To use the matrix tensioner, the dentist first rotates the adjustment screw 18 to bring the post 14 close to the post 12. The matrix band material is doubled and may be passed through the desired half of the transverse slot 29, then turning the band into the slot 28 on the bottom of the post 14 and the free ends are passed through a convenient leg of the V slot 26 on the bottom of post 12 and attached to the post by the locking screw 24. Alternatively, if it is too difficult to pass the doubled matrix band through half of the transverse slot 29 and then turn it and pass it through the half of slot 28, it may be passed completely through a transverse slot 28 and then passed into the "V" slot 26 in the bottom of post 12, as shown. The large loop in the matrix band produced from the slot 28 in the post 14 encircles a tooth and the adjustment screw 18 is then rotated to separate the two posts 12, 14 whereby the loop diameter is reduced to tighten the matrix around the tooth.

Figure 4:
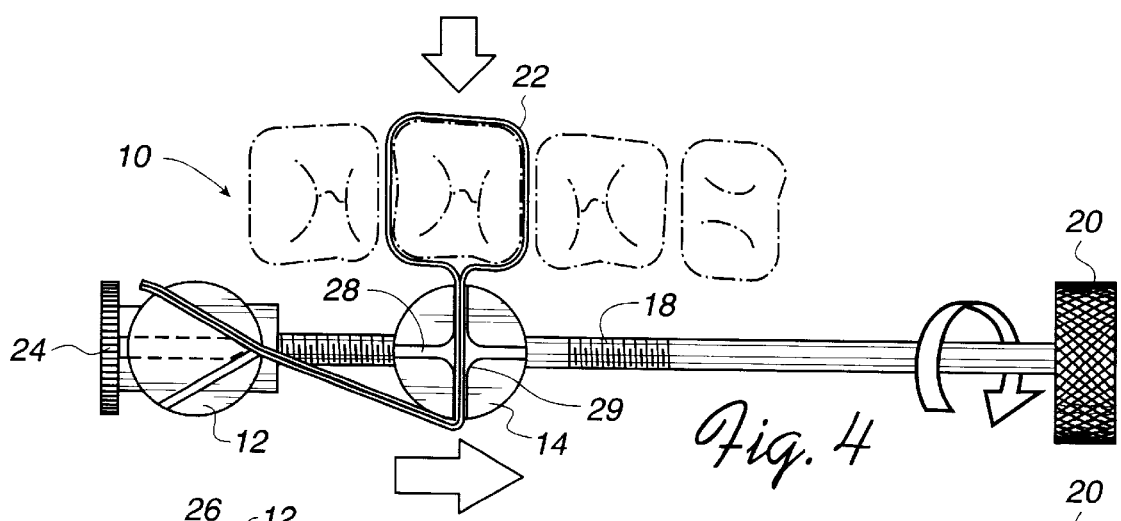
FIGS. 4 and 5 are bottom plan views thereof showing the matrix being tightened around a tooth shown by broken lines.
Figure 5:
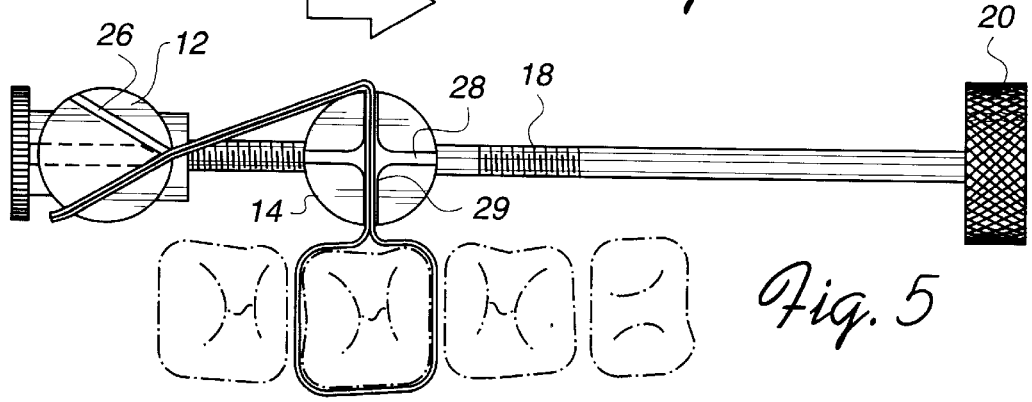

FIGS. 4 and 5 are bottom plan views of the matrix tensioner positioned adjacent teeth, such as molars. FIG. 4 illustrates the matrix tensioner 10 retaining a tooth on one side of the jaw and FIG. 5 illustrates the tensioner 10 retaining an adjacent tooth on the opposite side of the jaw. When the post 14 is positioned close to the post 12, the matrix band is loose and can easily be slipped over a tooth. After the dentist had encircled the tooth with the matrix band the adjustment screw is rotated to separate the post 14 from the post 12 thereby tightening the matrix around the tooth thus permitting the dentist to proceed.

Figure 6:
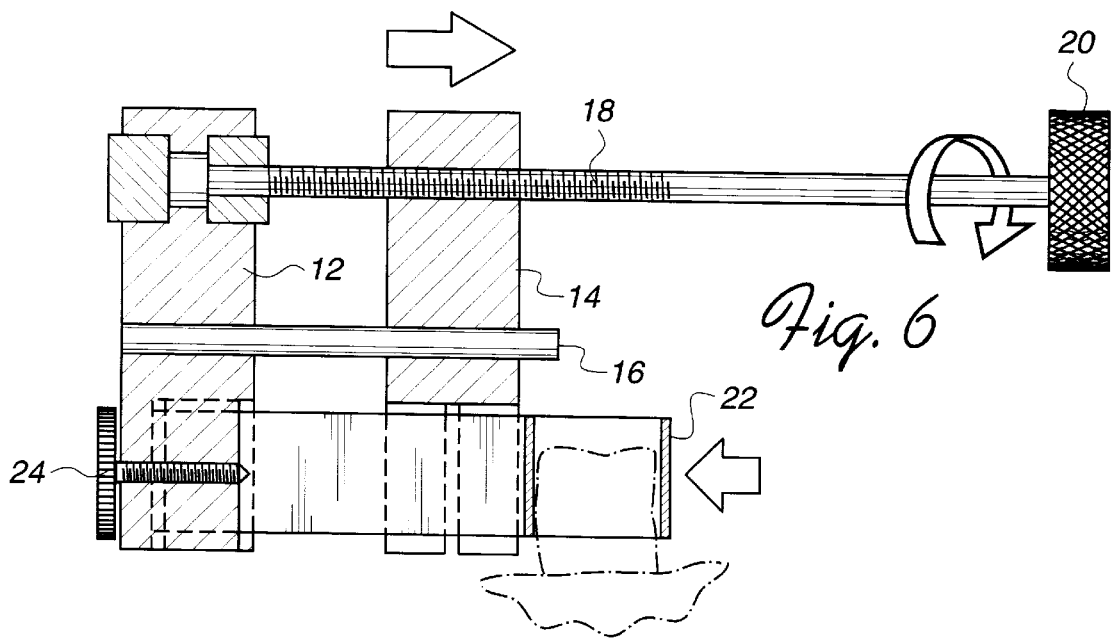
FIG. 6 is a sectional side elevational view of the tensioner showing is being tightened around a tooth shown by broken lines.

FIG. 6 is an elevational view showing the use of the matrix tensioner retaining an "in-line" tooth.

Thus the matrix tensioner is very versatile and is able to apply a matrix to nearly every tooth with little movement of the tensioner. It is easily adjustable extra-orally and its position on the lingual side of the tooth won't interfere with the dentist's procedure. Furthermore, the tensioner is easy to sterilize and is safe for use by both the dentist and patient

What is claimed is:

1. A matrix tensioner for tightly securing a matrix band around teeth, said matrix tensioner comprising:

a first post having first and second ends, said first end having a clamping means for securing both ends of a matrix band and occupying approximately one third of a first end of said post;

a second post of approximately the same dimension as said first post, said second post having first and second ends and axial right angle cross slots in approximately one third of a first end, each of said cross slots having a width for the easy passage of a double thickness of the matrix band;

first and second parallel rods passing through the diameters of said first and second posts at a right angle to the axis of said posts, said first rod being pivotally coupled to said first post and threaded through said second post for adjusting the space between said posts, said second rod being coupled to said first post and slideable through a hole in said second post for maintaining said posts parallel, one of said parallel rods being near said second end and one parallel rod located approximately midway between said first and second end of said first and second post, the distance between the rod at said midway point and the first end of the post being greater than the height of a patient's tooth on the lingual side of the jaw.

2. The matrix tensioner claimed in claim 1 wherein said clamping means on said first post includes a "V" shaped slots in said first end, the apex of said "V" pointing toward said second post, said clamping means further including a clamping screw through said post and engaging a matrix band in said apex, said slots in said "V" having widths for the passage of a double width of matrix band.

3. The matrix tensioner claimed in claim 2 wherein the cross slots in said second post are aligned so that one slot is parallel with the axis of the first and second parallel rods and one slot is a transverse slot.

4. The matrix tensioner claimed in claim 3 wherein the intersection of the parallel slot and the transverse slot is rounded to reduce friction on a matrix being tightened.

5. The matrix tensioner claimed in claim 3 wherein said first rod is pivotally coupled to said first post and is threaded through a threaded hole adjacent the second end of said second post, and said second rod is a guide rod secured to said first post and passes through a guide hole in the diameter of said second post.

6. The matrix tensioner claimed in claim 5 wherein said first rod is threaded and is provided with a handle means for manually adjusting the spacing of said first and second posts by the rotation of said first rod.

* * * * *